United States Patent [19]
Honkura et al.

[11] Patent Number: 5,103,173
[45] Date of Patent: Apr. 7, 1992

[54] PERMEAMETER HAVING A DIFFERENTIAL TRANSFORMER PROBE WITH A REDUCED DISTANCE BETWEEN THE DETECTING COILS

[75] Inventors: Yoshinobu Honkura; Hideki Fujii, both of Aichi; Hideo Arakawa; Kazumasa Sumi, both of Nagoya, all of Japan

[73] Assignees: Aichi Steel Works Ltd.; Kebushiki Kaisha Toyota Chuo Kenkyusho, both of Aichi, Japan

[21] Appl. No.: 663,661

[22] Filed: Mar. 4, 1991

[30] Foreign Application Priority Data

Mar. 5, 1990 [JP] Japan .................................. 2-54753

[51] Int. Cl.⁵ ...................... G01N 27/72; G01R 33/12
[52] U.S. Cl. .................................. 324/239; 324/222; 324/225; 324/233
[58] Field of Search ............... 324/222, 223, 225, 233, 324/239, 241

[56] References Cited

FOREIGN PATENT DOCUMENTS 59-20114 5/1984 Japan .

*Primary Examiner*—Walter E. Snow
*Attorney, Agent, or Firm*—Oliff & Berridge

[57] ABSTRACT

Permeameter suited for measuring permeability of a small, non-magnetic (i.e., the permeability value is close to 1) object. The probe of the permeameter is of the differential transformer type with an exciting coil and two detecting coils placed at both ends of the exciting coil. The difference in the outputs of the detecting coils is analyzed and the effect of the eddy current is effectively eliminated, whereby the signal representing the permeability of the object is extracted from the difference signal by the phase shift analysis. By reducing the distance between the two detecting coils, the influence of the disturbance of the eddy current at the boundary of the object sample is minimized and the permeameter can measure a small object sample without sacrificing accuracy and sensitivity.

11 Claims, 7 Drawing Sheets

PERMEAMETER HAVING A DIFFERENTIAL TRANSFORMER PROBE WITH A REDUCED DISTANCE BETWEEN THE DETECTING COILS

The present invention relates to an instrument for measuring magnetic permeability of non-magnetic (i.e., the relative permeability is close to unity) metallic material such as austenitic stainless steels.

BACKGROUND OF THE INVENTION

Austenitic stainless steels have superior corrosion resistance and heat resistance so that they are used in various fields such as chemical plants, petroleum plants, nuclear plants, aircraft, vessels, automobiles, buildings, electric appliances, home appliances and so on. Since, besides that, austenitic stainless steels are non-magnetic, they are also used in such parts where both strength and non-magnetism are required, e.g., mechanical parts of various electronic meters, a micro-shaft of a video tape recorder (VTR), a magnet roller of a printing machine, a shaft and a case of a magnetic valve.

The 18-8 stainless steel (JIS [Japanese Industrial Standards] SUS 304) and high-manganese stainless steel (ASTM 205) are typical non-magnetic austenitic stainless steels. The 18-8 stainless steel is a low carbon steel including about 18% chromium and about 8% nickel. Since the chemical composition is close to the border of the austenite region in the phase diagram, the 18-8 stainless steel is in a semi-stable state. Therefore, martensite is easily generated in a cold forming process and $\delta$-ferrite is easily generated when the balance in the chemical composition is fluctuated. Since martensite and $\delta$-ferrite are ferromagnetic, austenitic stainless steel including these phases acquires slight ferromagnetism, which loses one of its important merits.

As naturally understood, permeability of the austenitic stainless steel is related to the amount of these ferromagnetic phases. In order to assure the non-magnetic quality of their products, stainless steel manufacturers and part makers using non-magnetic stainless steel measure the permeability of the product. When the measured permeability value is greater than a predetermined value, the microstructure of the material steel is examined to determine the cause of the high permeability. If it is mainly caused by $\delta$-ferrite, the composition of the stainless steel is modified by adding austenite forming elements (i.e., elements that stabilize the austenite phase) such as nickel (Ni), carbon (C), nitrogen (N), etc., or the steel is heated for a long time at a high temperature before rolling to decompose the $\delta$-ferrite. If the main cause of the high permeability is determined to be martensite, the austenite forming elements as described above are added or the steel making process is properly modified.

In order to examine the microstructure of metal material, one should prepare a sample for microscopic inspection: first cut out a small piece of metal sample, polish it, and etch it with a proper acid solution. The determination of the martensitic phase and $\delta$-ferrite phase is difficult and the quantification of the content in the microscopic field requires complex calculations. That is the reason why convenient and short time measurement of permeability (which is related to the amount of the ferromagnetic phase) of metals has long been desired.

There are some other methods for measuring permeability of metal material. One is a magnetic balancing method in which an object sample piece and a reference non-magnetic sample piece are balanced and the same magnetic field is applied to both sample pieces. The magnetic balancing method is difficult to use in the field and the measurement cannot be made in a short time.

The inventors of the present invention have already developed a permeability measuring instrument (permeameter) that can be used in the field and can measure the permeability non-destructively (i.e., without preparing a small inspection sample) and in a short time (Japanese Published Examined Patent Application No. 20114/1984).

Recent trend in miniaturization of electronic devices requires smaller mechanical parts. For example, a micro-shaft used in a VTR is becoming smaller as the VTR itself is shrinking. The demand for non-magnetism is also becoming strict: the permeability value is required below 1.01 or 1.02. That is, a new permeameter is required that can measure a small object with high sensitivity (e.g., resolution of smaller than 0.001) non-destructively and easily.

The working principle of the permeameter described above is the magnetic induction phenomenon of an object metallic material. The probe of the permeameter is made from a ferromagnetic core rod and an exciting coil and two detecting coils wound thereon.

For example, for a cylindrical sample, the diameter needs more than 10 mm to correctly measure the permeability value with the permeameter described above. Microshafts used in current small-size VTRs are about 2 mm in diameter, and the demand for the non-magnetism is, as described above, below 1.01 or 1.02 in the permeability value.

In another prior art, an exciting coil and a detecting coil are combined to make a unit, and two such units are wound on the core rod to make a differential-transformer-type probe. In one type of the permeameter, in order to align the magnetic flux in the core rod straight as long as possible, the two coil units are placed at both ends of the core rod so that the inter-coil distance be as large as possible. In this type of permeameter, it is especially difficult, as described later, to measure the permeability value of a small sample accurately.

SUMMARY OF THE INVENTION

One object of the present invention is therefore to provide a permeameter that can measure a sample non-destructively.

Another object of the present invention is to provide a new permeameter that can measure permeability of a sample in the fields, i.e., a portable permeameter.

Still other object of the present invention is to provide a permeameter that can measure a small sample with high accuracy.

These and other objects are achieved by the permeameter of the present invention. The permeameter according to the present invention is suited especially for measuring a permeability value of a small object sample. The permeameter comprises following elements (FIG. 2):

(a) a differential-transformer-type probe 2, as schematically shown in FIG. 1, including
   (i) a ferromagnetic core rod 10 for contacting the object sample 1 with an end 13,
   (ii) an exciting coil 11 wound on the core rod 10, and
   (iii) two detecting coils 12 wound around the core rod 10 and at both sides of the exciting coil 11, where the distance $L_{CC}$ (mm) between the two detecting coils, frequency $f_{EX}$ (kHz) of an exciting current $I_{EX}$ flowing through the exciting coil 11 and the effective diameter $\Phi$ (mm) of the object sample 1 have the relation $$L_{CC} \leq f_{EX} + c \cdot \Phi \quad (c: \text{ a constant}), \tag{1}$$

(b) a signal processor 3 for analyzing the phase of a detecting signal from the detecting coils 12 of the probe 2 and extracting an output signal from the detecting signal corresponding to the permeability value of the object sample 1, (c) a reference signal generator 5 for generating the exciting current supplied to the exciting coil 11 and a reference signal supplied to the signal processor 3 for analyzing the phase of the detecting signal, and (d) an output device 6 for displaying the output signal.

Here the effective diameter $\Phi$ (mm) is the diameter of the object sample (if the measured surface of the sample is circular) whose permeability value is correctly measured by the permeameter. If the measured surface is not circular, the smallest distance from the probe to the boundary is regarded as the effective diameter $\Phi$.

The diameter of the core rod 10 is preferably less than the effective diameter $\Phi$ of the object sample 1. More accurate measurement will be ensured by shaping the end 13 of the core rod for contacting the object sample spherical and making the radius of the end sphere equal to or smaller than the radius of the core rod 10.

The output device 6 may include a signal converter for converting the output signal from the signal processor 3 to a permeability signal whose magnitude is proportional to the permeability of the object sample 1, whereby the operator can read the permeability value directly on a display (e.g., an analog voltage meter or a digital voltage meter) of the output device.

The operation of the permeameter is as follows. The phase of the output signal from the detecting coils 12 of the probe 2 is first analyzed in the signal processor 3 using the reference signal from the reference signal generator 5, and the shift in the phase of the output signal (or rotation of the signal from the reference vector) is detected. The phase shift in the output signal bears the information of the permeability of the object sample. The condition (a) for the probe is imposed because of the following reason.

Since the two detecting coils 12 of the probe 2 are constructed as a differential transformer type, the difference in the outputs of the two detecting coils 12 is the sum of following three factors:

(1) difference due to the magnetic flux within the core rod generated by the exciting coil 11, which is zero, (2) difference due to the magnetic flux within the object sample 1, which depends on the permeability of the material of the object sample 1, and (3) difference due to an eddy current generated in the object sample 1, which depends on the conductance of the object material.

In order to measure the correct permeability value of the object material, it is necessary to eliminate the factor (3) due to the eddy current from the difference in the outputs of the two detecting coils 12.

When the object sample is large enough so that the shape of the eddy current is not disturbed, the factor (3) due to the eddy current is adequately eliminated by the phase shift analysis in the signal processor 3, however large the difference in the output signals becomes due to the eddy current.

But when the size of the object sample 1 is not so large that the eddy current is restricted and disturbed by the edge of the object sample 1, the factor (3) cannot be adequately eliminated by the phase shift analysis alone.

The probe of the permeameter according to the present invention is therefore designed so that the distance $L_{CC}$ between the two detecting coils 12 (inter-coil distance) are small in order to obtain the information of a limited small area around the end tip 13 of the core rod 10 in which the eddy current is not disturbed by the edge of the object sample 1. As illustrated in FIG. 12, the part of an output of a detecting coil 121 or 122 corresponding to an observation site A depends on the area of the observation site A and the distance L1 or L2 between the observation site A and the respective detecting coil 121 or 122. Therefore, the difference in the two outputs of the two detecting coils 121 and 122 becomes almost zero for the observation site A located far from the probe tip 13, because $L1 \approx L2$ at the far site A.

When the inter-coil distance $L_{CC}$ is made smaller, the relation $L1 \approx L2$ holds to a nearer site, which means that an accurate permeability measurement can be made for a smaller object sample by effectively eliminating the factor of the eddy current.

In addition to reducing the inter-coil distance $L_{CC}$, it is effective to reduce the distance $L_{CO}$ between the lower detecting coil 122 and the surface of the object sample 1 (i.e., the length of the core rod 10 extending from the coil unit). It is preferable of course to equalize the extending lengths of the core rod 10 at both ends in order to improve the measurement accuracy because the magnetic condition is better balanced between the ends. The measurement accuracy is further improved by making the diameter $d_{PR}$ of the core rod 10 smaller than the diameter $\Phi$ of the object sample 1, because the size of the eddy current becomes smaller.

The difference $\Delta H$ in the magnitude of the magnetic fields at the center of the two detecting coils 121, 122 is calculated as:

$$\Delta H = -(a^2 \cdot i)/\{2 \cdot (a^2 + L_{CC}^2)^{3/2}\} + i/(2 \cdot a)$$

where i is the magnitude of the eddy current and a is the radius of the eddy current. The above formula shows that $\Delta H$ becomes smaller by reducing the inter-coil distance $L_{CC}$, which means that the component of the output due to the eddy current decreases and thus the measurement error is reduced.

When, on the other hand, the frequency $f_{EX}$ of the exciting current provided to the exciting coil 11 is increased, the depth of the eddy current in the object sample 1 becomes smaller due to the skin effect. Therefore, increasing the frequency $f_{EX}$ of the exciting current is another way of enabling an accurate permeability measurement of a small sample.

The condition $$L_{CC} \leq f_{EX} + c \cdot \Phi \quad (c: \text{ a constant})$$

for the probe as described above is thus obtained through experiments according to the above idea. The condition ensures that the resolution of the measurement (i.e., the smallest measurable difference) is about 0.001 in the permeability value for the effective diameter Φ of the object sample.

More detail and other features of the present invention is described with the description of embodiments thereof that follows.

BRIEF DESCRIPTION OF THE ATTACHED DRAWINGS

DETAILED DESCRIPTION OF PREFERRED EMBODIMENTS

Figure 7:
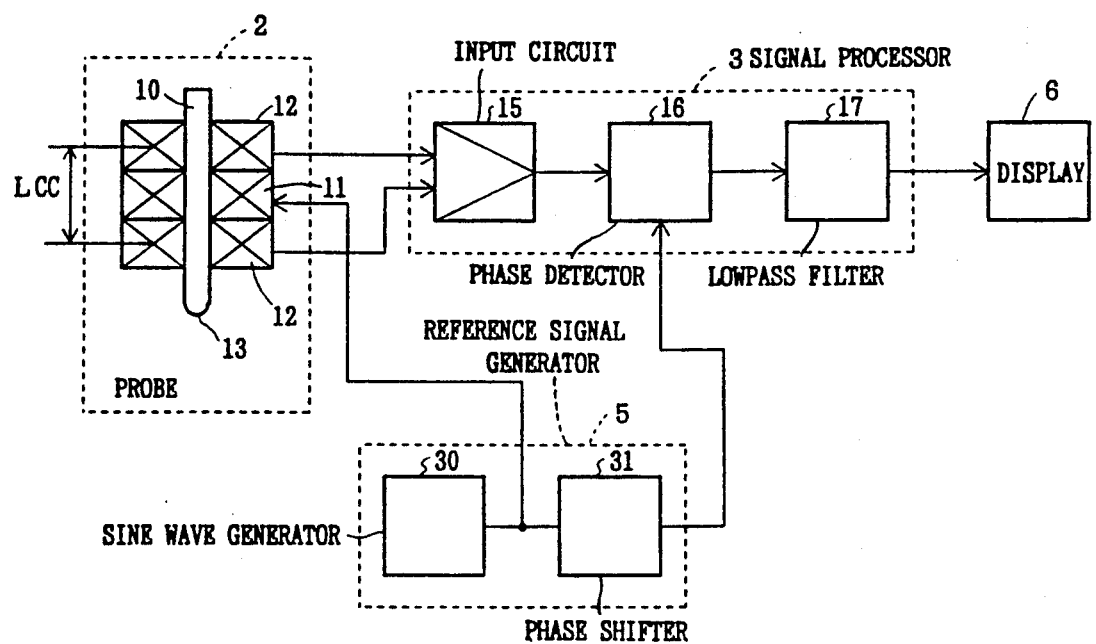
FIG. 7 is a detailed block diagram showing the structure of a permeameter according to the present invention.

An embodiment of the present invention is now described referring to FIG. 7. The permeameter of the present embodiment is also composed of a probe 2, a signal processor 3, a reference signal generator 5 and a display 6. The signal processor 3 includes an input circuit 15, a phase detector 16 and a low-pass filter 17. The input circuit 15 adds signals from the two detecting coils 12 and amplifies the added signal. Since the probe is differential transformer type, the turning direction (polarity) of the two detecting coils 12 are opposite to each other, and the addition of the outputs of the signals of the two detecting coils 12 is actually the difference between them. The reference signal generator 5 includes a sine wave generator 30 and a phase shifter 31.

The operation of the permeameter of the present embodiment is now described. First, the probe 2 is removed apart from any object, and an exciting AC current is provided to the exciting coil 11. At this time, the electromagnetic balance of the probe 2 is adjusted to set the display 6 at the origin (initial balancing). Then the end 13 of a core rod 10 of the probe 2 is contacted on an object to be measured, and the altering magnetic field generated by the exciting coil 11 creates a magnetic circuit through the core rod 10 and the object 1, and induces eddy current on the surface of the object 1. The non-unity permeability (permeability not equal to 1) and the eddy current of the object break the electromagnetic balance of the probe 2 adjusted before. As a result, a new signal is added (in the sense of vector addition) to the original induction current generated in the detecting coils 12. The original induction current is a current generated by the mutual induction of the exciting coil 11 and the detecting coils 12 at the initial balancing, and the vectorically added new signal bears information of the two parameters (the permeability of the object material and the eddy current).

The resultant induction currents from the detecting coils 12 are supplied to the signal processor 3, where the signal are first added and amplified by the input circuit 15. The signal is then analyzed by the phase detector 16: i.e., the signal is compared with a reference signal from the phase shifter 31 of the reference signal generator 5 and the shift in the phase is determined. Among the two parameters, the one relating to the eddy current is eliminated from the signal by the phase detector 16 and the other one relating to the permeability of the object material remains. The signal now representing the permeability of the object material then passes through the low-pass filter 17 to be a DC voltage signal and is visibly shown by the display 6 (e.g., an analog voltage meter or a digital voltage meter). Thus the permeameter of the present embodiment can measure the permeability of the object by simply touching the object surface with the probe end 13. The measuring operation is easy and measuring time is short, and the object need not be cut out into a small sample. Further, the permeameter can measure permeability of a very small object with high accuracy.

The sensitivity of a permeameter is improved (i.e., the resolution is made smaller) by:

i) Increasing the exciting current $I_{EX}$ or increasing the number of turns N1 of the exciting coil, or ii) Increasing the total number of turns N2 of the detecting coils 12. The inventors of the present invention made an intensive research and found that the resolution of a permeameter can be less than 0.001 when the above parameters I, N1 and N2 satisfy the following condition:

$$N1 \cdot N2 \cdot I_{EX} \geq 1000.$$

Figure 1:
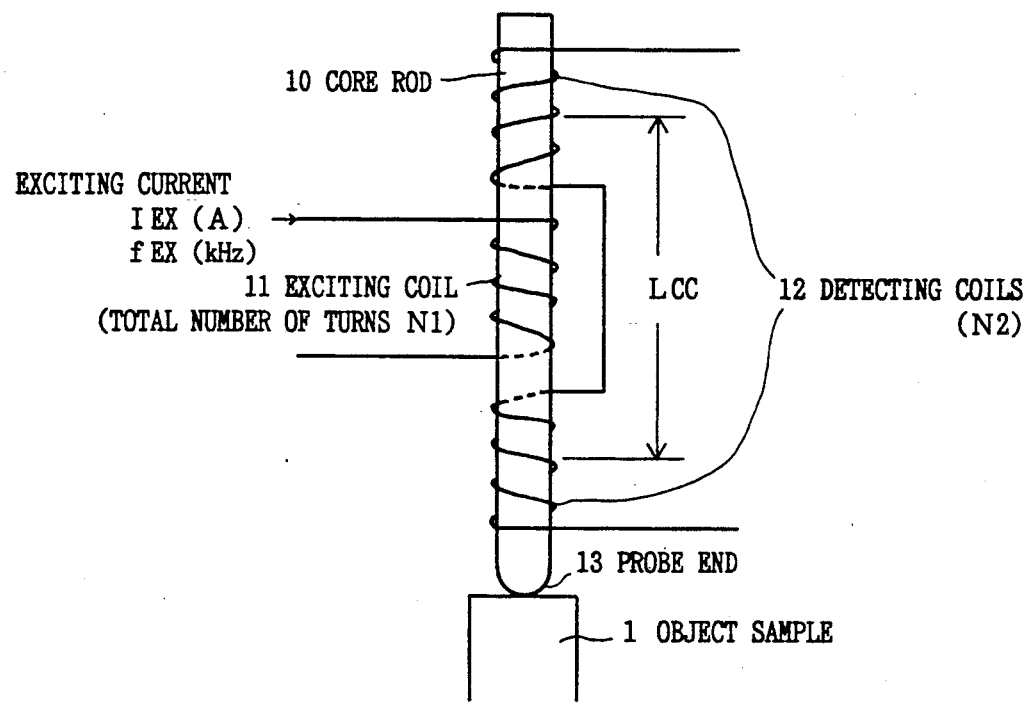
FIG. 1 is a schematic side view of a probe of a permeameter according to the present invention contacting an object sample.
Figure 2:
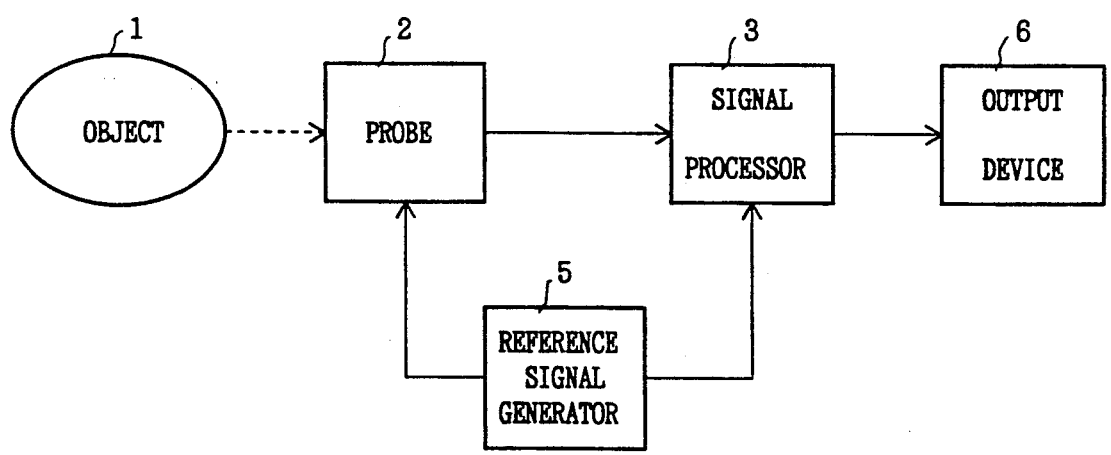
FIG. 2 is a block diagram illustrating the structure of the permeameter of the present invention.
Figure 3:
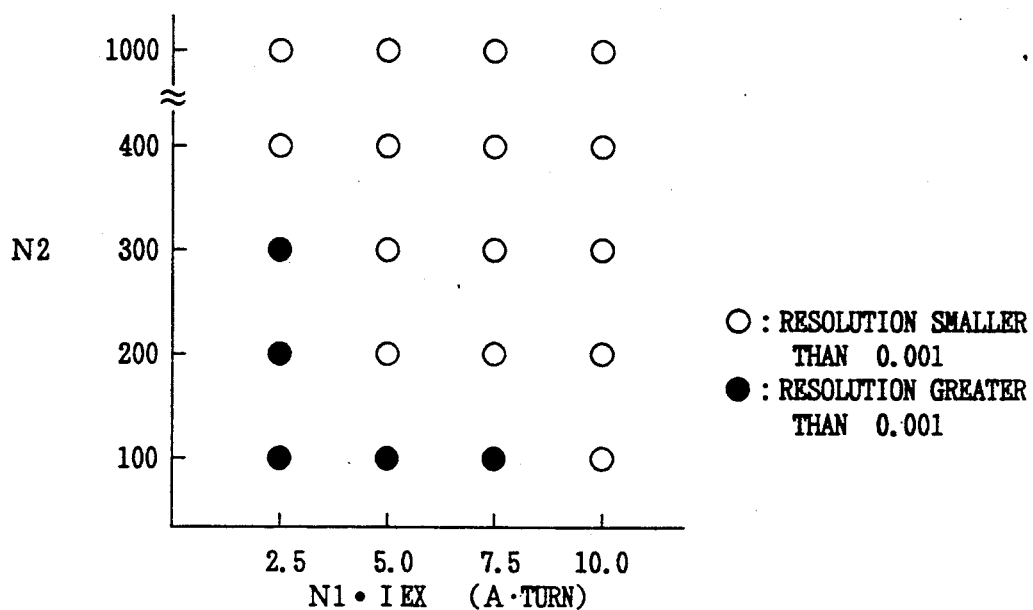
FIGS. 3 and 4 are graphs showing the relationship between sensitivity of a permeameter and various parameters thereof.

By satisfying the above inequality, a permeameter can measure a small object (e.g., diameter of about 2 mm) with a sufficient accuracy. A concrete example is now described referring to FIG. 3. Permeability of the same object is measured with probes having various values of I, N1 and N2, and the result is shown in the graph of FIG. 3 with the abscissa as $N1 \cdot I_{EX}$ and the ordinate as N2. In the graph of FIG. 3, the open circles denote that the resolution of the permeability is smaller than 0.001 (i.e., high sensitivity) and the solid circles denote that the resolution is larger than 0.001 (i.e., low sensitivity). The graph clearly shows that the permeameter has a resolution of 0.001 when the inequality $$N1 \cdot N2 \cdot I_{EX} \geq 1000$$

holds.

Figure 4:
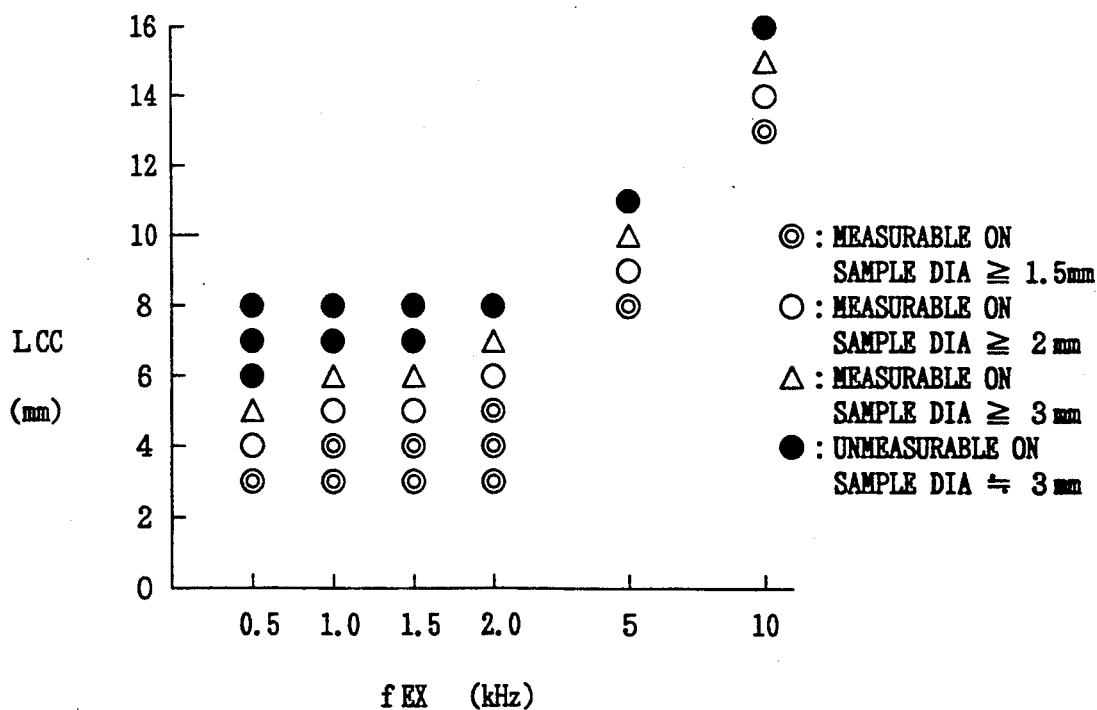

Next, permeability is measured on standard samples (whose permeability values are previously known) of various diameters Φ using a permeameter having various inter-coil distance $L_{CC}$ with various frequency $f_{EX}$ of the exciting current. The result is shown in FIG. 4 where: the double circles denote that the measured permeability value is equal to the known true value for samples of diameter larger than 1.5 mm; open circles denote that the measured permeability value is equal to the true value for samples of diameter larger than 2 mm; triangles denote that the measured permeability value is equal to the true value for samples of diameter larger than 3 mm; and solid circles denote that the measured permeability value is not equal to the true value for samples of diameter about 3 mm. FIG. 4 shows that if the inequality $$L_{CC} \leq f_{EX} + 4$$

is satisfied, the permeameter can measure a small sample of 2 mm diameter with sufficient accuracy, where the constant c is 2 in the above-described formula (1). If the frequency $f_{EX}$ of the exciting current is 1 kHz, the inter-coil distance $L_{CC}$ should be smaller than 5 mm according to the above formula. An actual example of the dimensions of the probe for measuring a sample of 2 mm diameter is: the diameter $d_{PR}$ of the core rod is 1 mm, the inter-coil distance $L_{CC}$ is 3.4 mm and the frequency is 1 kHz.

Figure 5:
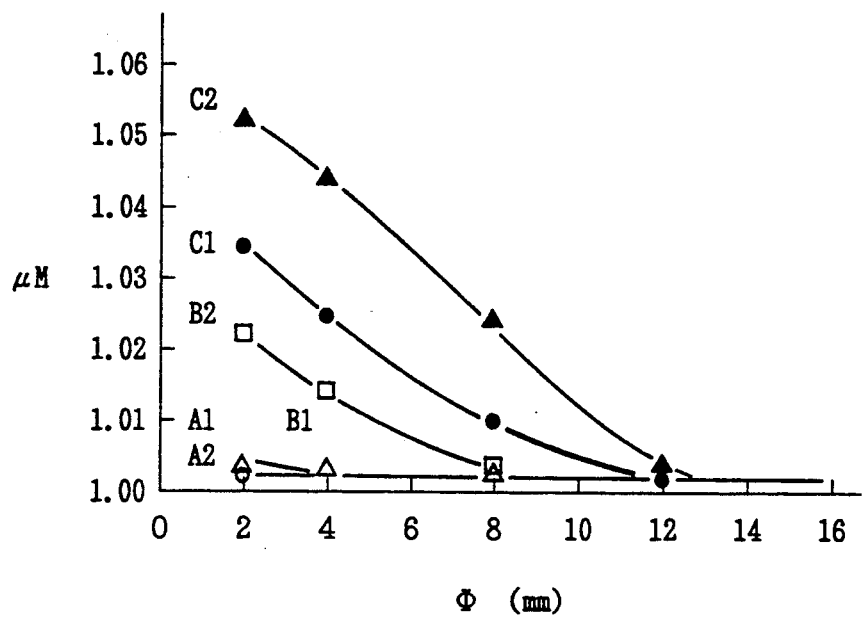
FIG. 5 is a graph showing permeability values of various samples measured by probes having various dimensions.

Another test is performed also to clarify the effect of the inter-coil distance $L_{CC}$ of the two detecting coils 12 on the measured value. The measurements are made with probes having various inter-coil distance $L_{CC}$ on standard cylindrical samples having diameter Φ of 2-16 mm and having known permeability value of 1.002. The result is shown in Table 1 and in FIG. 5, where A1 and A2 are probes according to the present invention, B1 and B2 are probes that do not satisfy the condition of the present invention, and C1 and C2 are conventional probes. The measurements are made with the condition that: the probe end (i.e., the end tip 13 of the ferromagnetic core rod 10) contacts the surface of the object sample; the frequency $f_{EX}$ of the exciting current is 1 kHz; the number of turns of the exciting and detecting coils N1, N2, and the exciting current $I_{EX}$ are fixed with the relation $N1 \cdot N2 \cdot I_{EX} = 3000$. FIG. 5 shows that the permeameter can measure smaller object (smaller diameter Φ) as the inter-coil distance $L_{CC}$ is made smaller. In concrete, the minimum diameter Φ that the conventional probe C1 and C2 can measure is 10 mm, while the probes A1 and A2 according to the present invention can measure object samples of 2 mm diameter.

Figure 6:
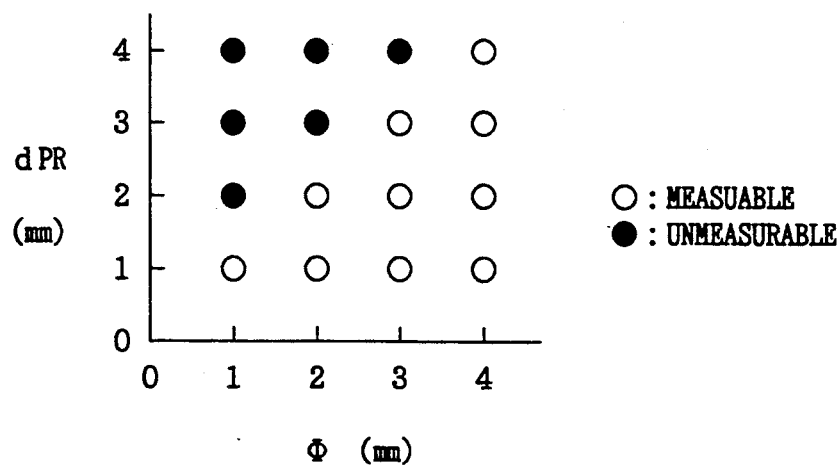
FIG. 6 is a graph showing the relationship between sensitivity of a permeameter and dimensions of the probe and sample.

The next test is for clarifying the effect of the diameter of the core rod 10 of the probe 2 on the sensitivity of the permeameter. Similarly to the previous test, the reference sample having diameter from 2 to 8 mm and known permeability value or 1.002 are measured using the probe with the core rod 10 having diameter of 1 to 4 mm. The number of turns of the exciting and detecting coils and the exciting current are fixed at $N1 \cdot N2 \cdot I_{EX} = 2000$ and the frequency of the exciting current is also fixed at $f_{EX} = 1$ kHz. The result is shown in FIG. 6 where the open circles denote that the measured value read on the display 6 is equal to the true value 1.002, and the solid circles denote that the measured value is not equal to the true value. FIG. 6 shows that the permeameter can measure a small size object correctly when the diameter of the core rod 10 is equal to or less than the diameter of the object.

Figure 9:
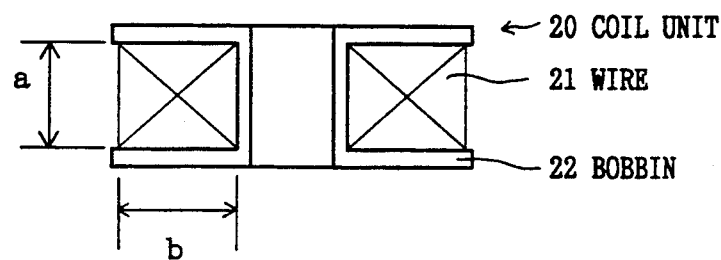
FIG. 9 is an enlarged view of a coil unit used in the embodiment of FIG. 7.
Figure 10:
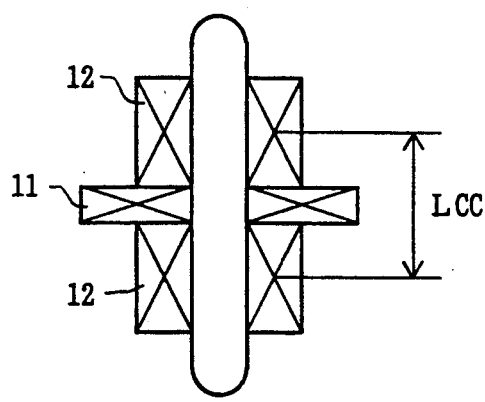
FIG. 10 is a schematic side view of another type of probe which has a small-height exciting coil for decreasing the intercoil distance.
Figure 13:
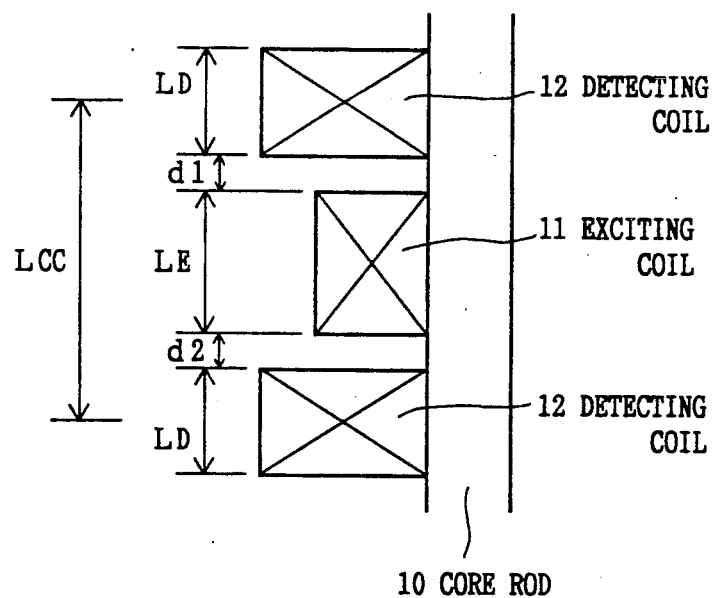
FIG. 13 is a schematic side view of a probe.

An enlarged cross-sectional view of the coil unit of the exciting coil 11 and the detecting coils 12 is shown in FIG. 9. The wire 21 is wound in a bobbin 22, and, in order to reduce the inter-coil distance $L_{CC}$, the axial dimension a of the coil unit 20 (especially that for the exciting coil 11) is made smaller than the radial dimension b. Another example of the coil configuration is shown in FIG. 10 where the inter-coil distance $L_{CC}$ is greatly reduced by making the exciting coil 11 intervening between the two detecting coils 12 flat-shaped. As shown in FIG. 13, the distance (clearance) d1 and d2 between the exciting coil and the detecting coils are also preferred to be small in order to shorten the inter-coil distance $L_{CC}$. A preferred condition for the clearances d1 and d2 is:

d1 < $L_D$ or $L_E$, and d2 < $L_D$ or $L_E$.

Most preferably, the clearances d1 and d2 are as small as the thickness of the end walls of the adjacent bobbins so that adjacent coil units are placed in contact with each other.

It is preferable to use a thin wire 21 in order to increase the number of turns N1 and N2 without increasing the size of the coil unit 20, and improve the sensitivity of the permeameter (cf. the formula $N1 \cdot N2 \cdot I_{EX} \geq 1000$).

The core rod can be made of ferrite, Permalloy, or other high permeability (ferromagnetic) material, where Permalloy is preferred for better sensitivity.

Figure 8:
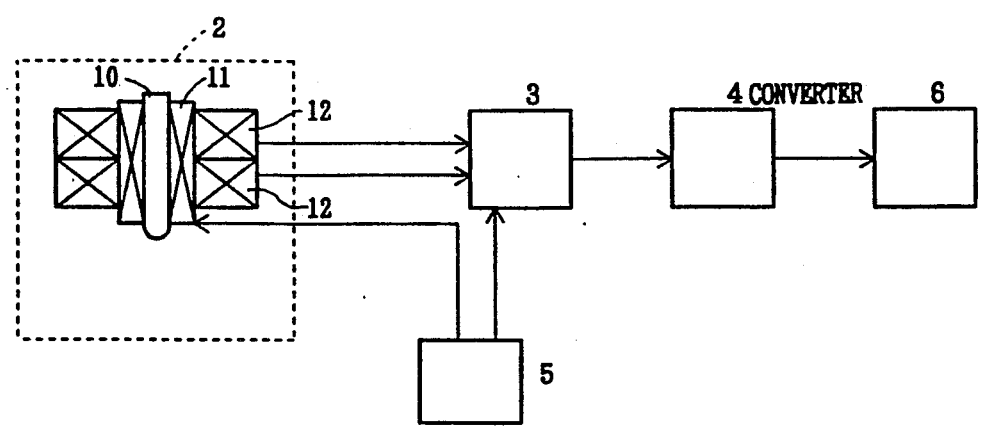
FIG. 8 is a detailed block diagram showing the structure of another permeameter according to the present invention.

A different type of permeameter according to the present invention is shown in FIG. 8. The probe 2 of this embodiment has a different structure from that of the previous embodiment (FIG. 7), and a converter 4 is inserted between the signal processor 3 and the display 6. While, in the previous embodiment, the display 6 showed a voltage value, the converter 4 converts the DC voltage value to the value proportional to the permeability of the object, thus enabling the operator directly reading the permeability value on the display 6. In the probe 2 of this embodiment, an exciting coil 11 is first wound on almost the entire length of the core rod 10, and then the two detecting coils 12 are wound on the exciting coil 11, making a differential-transformer-type probe. This probe structure allows shorter inter-coil distance $L_{CC}$, which is more suited to satisfy the condition of the present invention.

Figure 11:
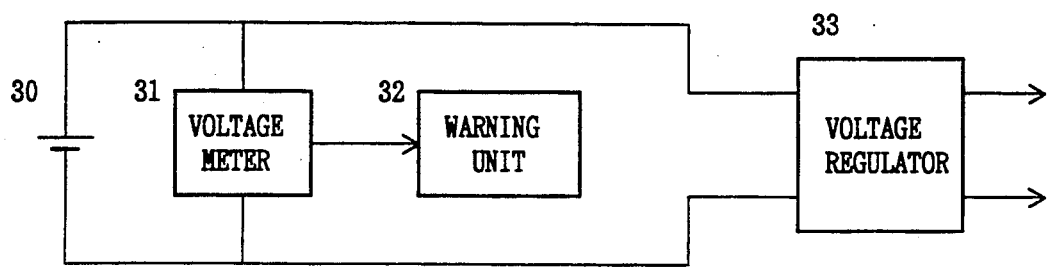
FIG. 11 is a circuit diagram of a battery-type power unit provided in a permeameter.
Figure 12:
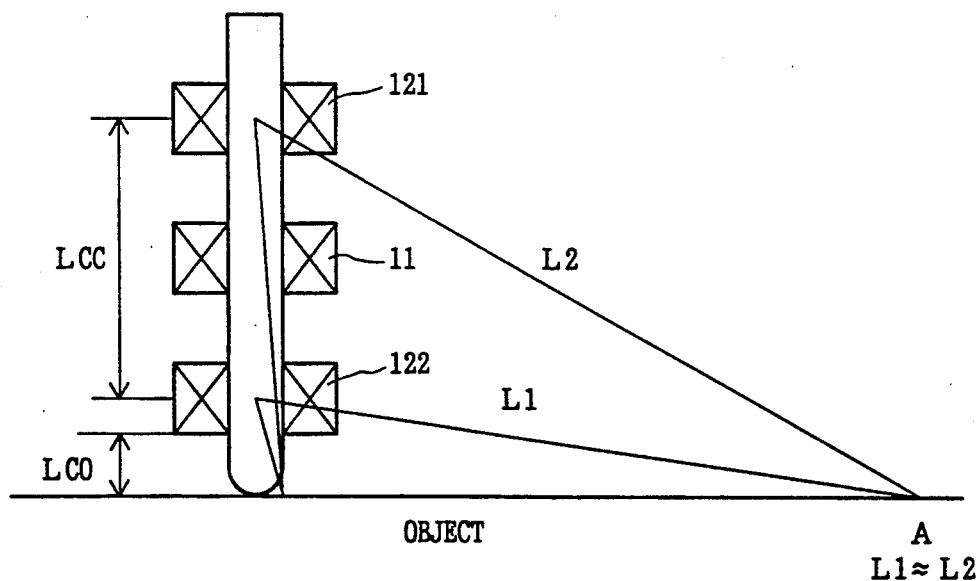
FIG. 12 is a schematic side view of a probe and a measurement object.

The permeameter can be powered either by the line or by a battery, but the battery power is preferred. When the permeameter is powered by a battery, the output of the permeameter is free from line noises and the measurement can be more stable because influence of the electrical potential of the object sample can be avoided. In this case, the permeameter is preferred to include a battery warning circuit as shown in FIG. 11. In this configuration, the battery power is supplied to the other units of the permeameter through a voltage regulator 33. In the mean time, the voltage of the battery 30 is detected by a voltage meter 31 and the detected voltage is compared with a preset value in a warning unit 32. When the battery voltage falls below the preset level, the warning unit 32 beeps or flashes.

TABLE 1

| No. | LCC (mm) | Φ (mm) | PERMEABILITY |
|---|---|---|---|
| A1 | 3 | 16 | 1.002 |
|  |  | 12 | 1.002 |
|  |  | 8 | 1.002 |
|  |  | 4 | 1.002 |
|  |  | 2 | 1.002 |
| A2 | 5 | 16 | 1.002 |
|  |  | 12 | 1.002 |
|  |  | 8 | 1.002 |

TABLE 1-continued

| No. | LCC (mm) | Φ (mm) | PERMEABILITY |
|---|---|---|---|
|    |    | 4  | 1.002 |
|    |    | 2  | 1.002 |
| B1 | 6  | 16 | 1.002 |
|    |    | 12 | 1.002 |
|    |    | 8  | 1.002 |
|    |    | 4  | 1.002 |
|    |    | 2  | 1.004 |
| B2 | 8  | 16 | 1.002 |
|    |    | 12 | 1.002 |
|    |    | 8  | 1.004 |
|    |    | 4  | 1.015 |
|    |    | 2  | 1.023 |
| C1 | 10 | 16 | 1.002 |
|    |    | 12 | 1.002 |
|    |    | 8  | 1.018 |
|    |    | 4  | 1.025 |
|    |    | 2  | 1.035 |
| C2 | 12 | 16 | 1.002 |
|    |    | 12 | 1.004 |
|    |    | 8  | 1.025 |
|    |    | 4  | 1.045 |
|    |    | 2  | 1.053 |

What is claimed is:

1. A permeameter for measuring a permeability value of an object sample, the permeameter comprising:
   (a) a differential-transformer-type probe including
      (i) a ferromagnetic core rod for contacting the object sample with an end,
      (ii) an exciting coil wound on the core rod, and
      (iii) two detecting coils wound around the core rod and at both sides of the exciting coil,
      where the distance $L_{CC}$ (mm) between the two detecting coils, frequency $f_{EX}$ (kHz) of an exciting current flowing through the exciting coil and the effective diameter $\Phi$ (mm) of the object sample have the relation:

$$L_{CC} \leq f_{EX} + c \cdot \Phi \quad (c: \text{a constant}),$$

(b) a signal processor for analyzing the phase of a detecting signal from the detecting coils of the probe and extracting an output signal from the detecting signal corresponding to the permeability value of the object sample,
   (c) a reference signal generator for generating the exciting current supplied to the exciting coil and a reference signal supplied to the signal processor for analyzing the phase of the detecting signal, and
   (d) an output device for displaying the output signal.

2. A permeameter as claimed in claim 1, where the value of the constant c is from 1.5 to 2.

3. A permeameter as claimed in claim 1, where the value of $L_{CC}$ is less than 4.

4. A permeameter as claimed in claim 1, where the output device includes a signal converter for converting the output signal from the signal processor to a permeability signal whose magnitude is proportional to the permeability of the object sample.

5. A permeameter as claimed in claim 1, where the end of the core rod of the probe for contacting the object sample is spherical whose radius is equal to or smaller than the radius of the core rod.

6. A permeameter as claimed in claim 1, where the clearance between the exciting coil and one of the detecting coils is smaller than the dimension of any one of the exciting coil and the detecting coils parallel to the axis of the core rod.

7. A permeameter as claimed in claim 1, where the dimension of the exciting coil parallel to the axis of the core rod is smaller than the dimension of the exciting coil parallel to the radius of the core rod, and the detecting coils are placed adjoining to both ends of the exciting coil.

8. A permeameter as claimed in claim 1, where the dimension of the detecting coil parallel to the axis of the core rod is smaller than the dimension of the detecting coil parallel to the radius of the core rod, and the detecting coils are placed adjoining to both ends of the exciting coil.

9. A permeameter as claimed in claim 1, where the two detecting coils are wound on the exciting coil which is wound on the core rod.

10. A permeameter as claimed in claim 9, where the dimension of the exciting coil parallel to the radius of the core rod is smaller than the dimension of the detecting coil parallel to the radius of the core rod.

11. A permeameter as claimed in claim 1, where the number of turns of the exciting coil N1, the total number of turns of the two detecting coils N2 and the amount of the exciting current $I_{EX}$ have the relation:

$$N1 \cdot N2 \cdot I_{EX} \geq 1000.$$

* * * * *